United States Patent
Xu et al.

(10) Patent No.: US 10,980,465 B2
(45) Date of Patent: Apr. 20, 2021

(54) SENSOR ASSEMBLY

(71) Applicant: Shenzhen Mindray Bio-Medical Electronics Co., Ltd., Shenzhen (CN)

(72) Inventors: Cong Xu, Shenzhen (CN); Bingyin Wang, Shenzhen (CN); Yangbo Liu, Shenzhen (CN); Zhigang Hu, Shenzhen (CN); Zhonghua Liu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 352 days.

(21) Appl. No.: 16/126,304

(22) Filed: Sep. 10, 2018

(65) Prior Publication Data
US 2019/0000341 A1    Jan. 3, 2019

Related U.S. Application Data

(63) Continuation of application No. PCT/CN2016/076428, filed on Mar. 15, 2016.

(51) Int. Cl.
*A61B 5/02*    (2006.01)
*H05K 1/14*    (2006.01)
(Continued)

(52) U.S. Cl.
CPC ........... *A61B 5/282* (2021.01); *G01N 27/041* (2013.01); *H05K 1/147* (2013.01); *H05K 5/0052* (2013.01);
(Continued)

(58) Field of Classification Search
CPC .. A61B 5/02; A61B 5/024; A61B 5/04; A61B 5/048; A61B 5/0408;
(Continued)

(56) References Cited

U.S. PATENT DOCUMENTS 5,494,043 A * 2/1996 O'Sullivan ........ A61B 5/02208
600/500
6,580,942 B1    6/2003 Willshire
(Continued)

FOREIGN PATENT DOCUMENTS

CN    204192610 U    3/2015
WO    WO2017/156716 A1    9/2017

OTHER PUBLICATIONS

Moinzaeh, "New Stealth Heart Monitor will help detect a leading cause of stroke," The Daily of the University of Washington, Nov. 2011, Student Publications, Seattle, WA, http://www.dailyuw.com/news/article_c5ccf5c5-174b-57d6-8246-1cldb98f713f.html.
(Continued)

*Primary Examiner* — Tuan T Dinh
(74) *Attorney, Agent, or Firm* — Kory D. Christensen

(57) ABSTRACT

A sensor assembly includes a housing and a circuit board assembly. The housing includes a first accommodation cavity, a second accommodation cavity, a first connection portion, a second connection portion, and a third accommodation cavity. The first connection portion is connected to the first accommodation cavity and one end of the third accommodation cavity, and the second connection portion is connected to the second accommodation cavity and the other end of the third accommodation cavity. The circuit board assembly is accommodated within the first accommodation cavity, the second accommodation cavity, the first connection portion, the second connection portion and the third accommodation cavity. The width of the first connection portion and the second connection portion is less than the width of the first accommodation cavity, the second accommodation cavity and the third accommodation cavity. The first connection portion and the second connection portion
(Continued)

are each provided with a buffer groove along the width direction.

14 Claims, 6 Drawing Sheets

(51) Int. Cl.
*A61B 5/282* (2021.01)
*G01N 27/04* (2006.01)
*H05K 5/00* (2006.01)

(52) U.S. Cl.
CPC . *A61B 2562/0209* (2013.01); *A61B 2562/043* (2013.01); *A61B 2562/164* (2013.01); *A61B 2562/166* (2013.01); *H05K 2201/10037* (2013.01); *H05K 2201/10151* (2013.01)

(58) Field of Classification Search
CPC . A61B 5/0478–0496; G01L 5/00; G01L 5/04; G01N 27/04; H05K 1/14; H05K 5/00
USPC .......... 361/748–750, 782–784, 803; 174/254–261, 350–355, 520–525
See application file for complete search history.

(56) References Cited

U.S. PATENT DOCUMENTS

| | | | |
|---|---|---|---|
| 7,206,630 B1* | 4/2007 | Tarler | A61B 5/398 600/509 |
| 8,214,007 B2* | 7/2012 | Baker | A61B 5/0006 600/372 |
| 10,123,582 B2* | 11/2018 | Crossman | G01L 5/14 |
| 2008/0091089 A1 | 4/2008 | Guillory et al. | |
| 2011/0077497 A1* | 3/2011 | Oster | A61B 5/274 600/372 |
| 2013/0245415 A1 | 9/2013 | Kumar et al. | |
| 2014/0094676 A1 | 4/2014 | Gani et al. | |
| 2015/0000370 A1 | 1/2015 | Crossman et al. | |
| 2015/0065840 A1* | 3/2015 | Bailey | A61B 5/0492 600/384 |
| 2015/0094559 A1* | 4/2015 | Russell | A61B 5/0022 600/391 |
| 2015/0141784 A1* | 5/2015 | Morun | G06F 3/015 600/372 |
| 2016/0045135 A1* | 2/2016 | Kim | A61B 5/6843 600/391 |

OTHER PUBLICATIONS

Supplementary Partial European Search Report, European Application No. EP 116 89 3881, pp. 1-5.

Novosense AB: "Novosense ECG technology," Jul. 7, 2014, Retrieved from the Internet: https://web.archive.org.web/20140707053337/ http://www.novosense.se:80/technology.html [retrieved on Feb. 24, 2021].

* cited by examiner

SENSOR ASSEMBLY

CROSS REFERENCE TO RELATED APPLICATIONS

This application is a continuation of PCT Application No. PCT/CN2016/076428, filed Mar. 15, 2016, for SENSOR ASSEMBLY, which is incorporated herein by reference.

TECHNICAL FIELD

The present disclosure relates to the field of physiological monitoring and, in particular, to a sensor assembly for monitoring physiological signs.

BACKGROUND

The measurement of bioelectricity (e.g., electroencephalogram, electrocardiogram, electromyography, etc.) has been widely applied in the monitoring and diagnosis of various nerve system diseases, as well as bioelectric feedback rehabilitation.

With the development of mobile Internet technology, electrocardiogram measurement and monitoring have become possible outside of the hospital. With regard to the current out-of-hospital electrocardiogram measurement and monitoring, real-time electrocardiogram measurements are performed on users by means of a wearable sensor assembly so as to enable motion monitoring and chronic disease management. Such wearable sensor assemblies are mainly for healthy or chronic patient groups, and this type of population typically has the ability to live independently and thus engage in more frequent motion in daily life. The motion of a wearer will cause the sensor assembly to produce motion artifacts during a measurement process, and the generation of artifacts greatly interferes with the collection of electrocardiogram signals. Therefore, reducing motion artifacts in a measurement process is a technical problem that needs to be solved by such sensor assemblies.

SUMMARY

The present disclosure provides a sensor assembly that reduces motion artifacts and improves electrocardiogram signal collection. One embodiment of the present disclosure provides a sensor assembly comprising a housing and a circuit board assembly, wherein the housing includes a first accommodation cavity, a second accommodation cavity, a first connection portion, a second connection portion and a third accommodation cavity, with the first connection portion being connected to the first accommodation cavity and one end of the third accommodation cavity, and the second connection portion being connected to the second accommodation cavity and the other end of the third accommodation cavity. The circuit board assembly is accommodated within the first accommodation cavity, the second accommodation cavity, the first connection portion, the second connection portion, and the third accommodation cavity, with the widths of the first connection portion and the second connection portion being less than the widths of the first accommodation cavity, the second accommodation cavity, and the third accommodation cavity.

The first connection portion and the second connection portion are each provided with a buffer groove along the width direction. In one embodiment, the third accommodation cavity is thicker than the first accommodation cavity and the second accommodation cavity.

A projected area of the third accommodation cavity in a plane where the circuit board assembly is located is greater than the projected area of the first accommodation cavity in the plane where the circuit board assembly is located, and the projected area of the third accommodation cavity in the plane where the circuit board assembly is located is greater than the projected area of the second accommodation cavity in the plane where the circuit board assembly is located.

The circuit board assembly includes a first measurement circuit board accommodated within the first accommodation cavity, a second measurement circuit board accommodated within the second accommodation cavity, a reference circuit board accommodated within the third accommodation cavity, a first flexible printed circuit board (FPCB) accommodated within the first connection portion and a second FPCB accommodated within the second connection portion, with one end of the reference circuit board being connected to the first measurement circuit board via the first FPCB, and the other end of the reference circuit board being connected to the second measurement circuit board via the second FPCB.

The reference circuit board includes a first reference circuit board, a second reference circuit board and a third FPCB, with the first reference circuit board being connected to the first measurement circuit board, the second reference circuit board being connected to the second measurement circuit board, and the first reference circuit board and the second reference circuit board being connected via the third FPCB.

The sensor assembly further includes a battery, wherein the battery is arranged on the third FPCB.

The housing includes an upper housing and a lower housing, with the upper housing and the lower housing mating to form the first accommodation cavity, the second accommodation cavity, the first connection portion, the second connection portion and the third accommodation cavity; and the circuit board assembly is arranged between the upper housing and the lower housing.

The buffer groove is arranged on the upper housing. The upper housing and the lower housing are integrally formed. The upper housing and the lower housing are made from a silica gel material.

The sensor assembly further includes a sensor accessory, wherein the sensor accessory includes a base material, and a first output electrode, a second output electrode, a third output electrode and a fourth output electrode which are sequentially arranged on one side of the base material, and a first input electrode, a second input electrode and a third input electrode which are sequentially arranged on the other side of the base material, with the first input electrode being electrically connected to the first output electrode, the third input electrode being electrically connected to the fourth output electrode, the second input electrode being electrically connected to the second output electrode and/or the third output electrode, and a center distance between the first input electrode and the third input electrode being greater than or equal to 60 mm.

A center distance between the first output electrode and the second output electrode may be 18-22 mm, a center distance between the second output electrode and the third output electrode may be 22-25 mm, and a center distance between the third output electrode and the fourth output electrode may be 18-22 mm.

The second output electrode and the third output electrode are electrically connected to the second input electrode simultaneously. The second input electrode is arranged between the first input electrode and the third input electrode.

The sensor assembly further includes a fourth input electrode arranged on the other side of the base material, wherein the fourth input electrode is electrically connected to the third output electrode; the second input electrode is electrically connected to the third output electrode; the base material is of an L shape, and the base material includes a first long arm and a second long arm; the first input electrode, the second input electrode and the third input electrode are sequentially arranged on the first long arm along a direction far away from the second long arm; and the fourth input electrode is arranged on the second long arm of the base material.

A center distance between the fourth input electrode and the first input electrode may be 70-90 mm. An included angle between the first long arm and the second long arm may be 90°-150°. A center distance between the second input electrode and the third input electrode may be 18-22 mm. A center distance between the first input electrode and the second input electrode may be 40-50 mm.

The sensor assembly further includes a sensor accessory, wherein the sensor accessory includes a base layer, a conductive layer formed on one side of the base layer, a barrier layer formed on the other side of the base layer, and a conductive gel attached to the barrier layer, with a conductive via hole penetrating the two sides of the base layer being arranged on the base layer, and the conductive layer being electrically connected to the barrier layer via the conductive via hole.

The sensor accessory further includes a connection layer, with a communication hole being arranged on the connection layer, and the side of the base layer provided with the conductive gel is attached to the connection layer, with the conductive gel being exposed via the communication hole.

The sensor accessory further includes a support layer, with the support layer being detachably attached to the connection layer, a through hole being arranged on the support layer, and the conductive layer being exposed via the through hole. In one embodiment, the shape of the through hole of the support layer is identical to the contour of the base layer.

The support layer and the connection layer are fixed to each other by means of vacuum adsorption. The connection layer includes a connection region and an edge region, wherein the connection region provides with the communication hole, and a thickness of the edge region less than 0.1 mm. The projection of the conductive gel on the barrier layer is contained in the barrier layer. The material of the barrier layer is silver or silver chloride. The base layer is made of one or more of a flexible PET, foam-back and non-woven material.

One embodiment of a method for manufacturing a sensor assembly may include: providing a circuit board assembly, and placing the circuit board assembly into a first mold cavity for a first injection molding to form a lower housing below the circuit board assembly, wherein the lower housing has a first bottom side, a second bottom side, a first connection bottom side, a second connection bottom side and a third bottom side; and taking the circuit board assembly from the first mold cavity, and then placing the circuit board assembly into a second mold cavity for a second injection molding to form an upper housing on the lower housing, wherein the upper housing has a first top side, a second top side, a first connection top side, a second connection top side and a third top side, the lower housing and the upper housing form a housing to accommodate the circuit board assembly.

During the process of placing the circuit board assembly into the first mold cavity for the first injection molding, the circuit board assembly is connected to an outer frame, such that the circuit board assembly is fixed the position within the first mold cavity by means of the outer frame.

In some embodiments, the process of taking the circuit board assembly from the first mold cavity and then placing the circuit board assembly into the second mold cavity for the second injection molding includes taking the circuit board assembly from the first mold cavity, removing the outer frame, placing the circuit board assembly into the second mold cavity, and fixing the circuit board assembly position within the second mold cavity by means of the lower housing.

A first accommodation cavity is formed between the first top side and the first bottom side, a second accommodation cavity is formed between the second top side and the second bottom side, a third accommodation cavity is formed between the third top side and the third bottom side, the first connection bottom side and the first connection top side form a first connection portion, the second connection bottom side and the second connection top side form a second connection portion, and the circuit board assembly is accommodated within the first accommodation cavity, the second accommodation cavity, the first connection portion, the second connection portion and the third accommodation cavity.

In the present disclosure, by setting the width of the first connection portion and the second connection portion of the housing to be less than the width of the accommodation cavity to which the two connection portions are connected, and arranging a buffer groove on the first connection portion and the second connection portion to make the flexibility of the connection portions better, and a plurality of accommodation cavities may make a relative motion following the motion of a muscle group without changing the positional relationship with the muscle group. Thus, during the motion of a user, the position of the muscle group detected by the sensor assembly is basically kept fixed, so as to reduce the motion artifact caused by the deformation of skin and the influence of the motion artifact on the monitoring, and improve the accuracy of physiological signal monitoring.

DETAILED DESCRIPTION

The technical solutions of the embodiments of the present disclosure will be described below clearly and comprehensively in conjunction with the drawings of the embodiments of the present disclosure. Clearly, the embodiments described are merely some embodiments of the present disclosure and are not all possible embodiments. Based on the embodiments given in the present disclosure, all other embodiments that would be obtained by those of ordinary skill in the art without expending inventive effort shall fall within the scope of protection of the present disclosure.

The ordinal determiners "first", "second", etc. used in the following embodiments of the present disclosure are merely the words for the purpose of clearly illustrating the difference of similar features in the present disclosure, but not represent the arrangement order or usage order of the corresponding features.

Figure 1:
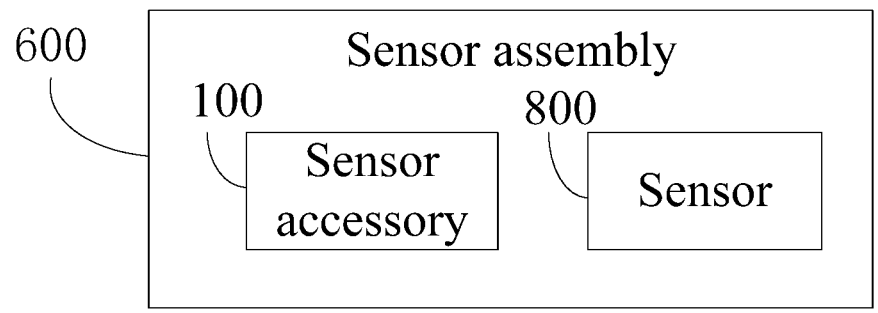
FIG. 1 is a modular schematic diagram of a sensor assembly.
Figure 2:
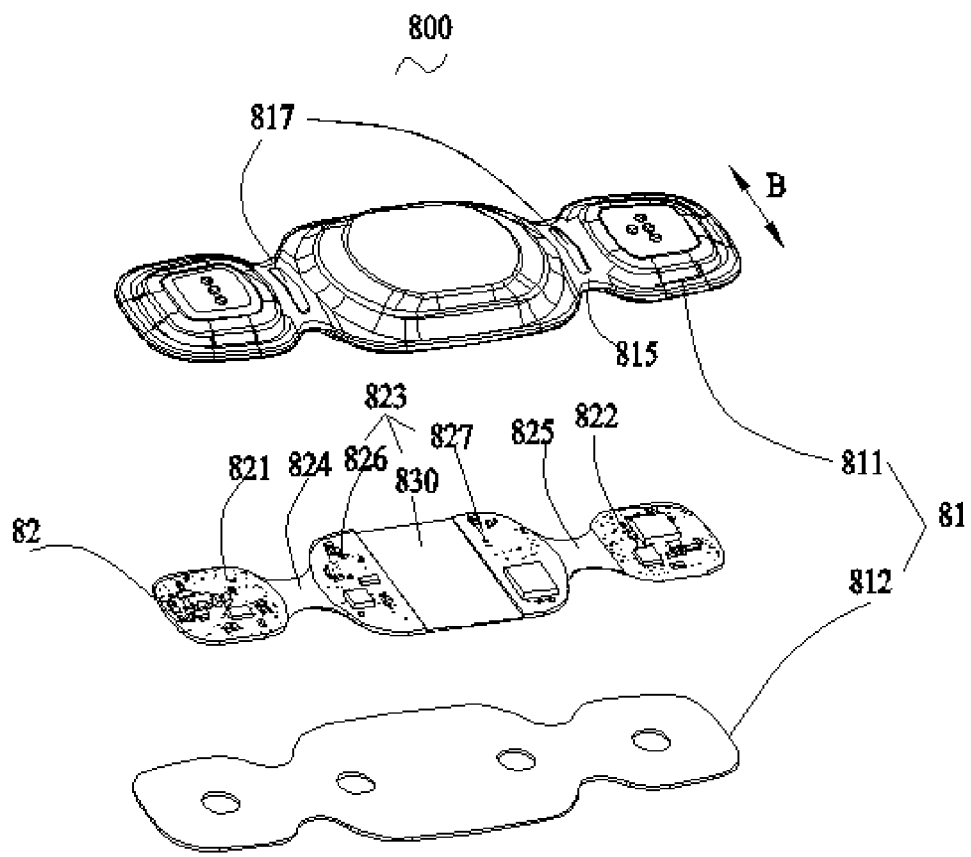
FIG. 2 is an exploded view of a sensor of FIG. 1.
Figure 3:
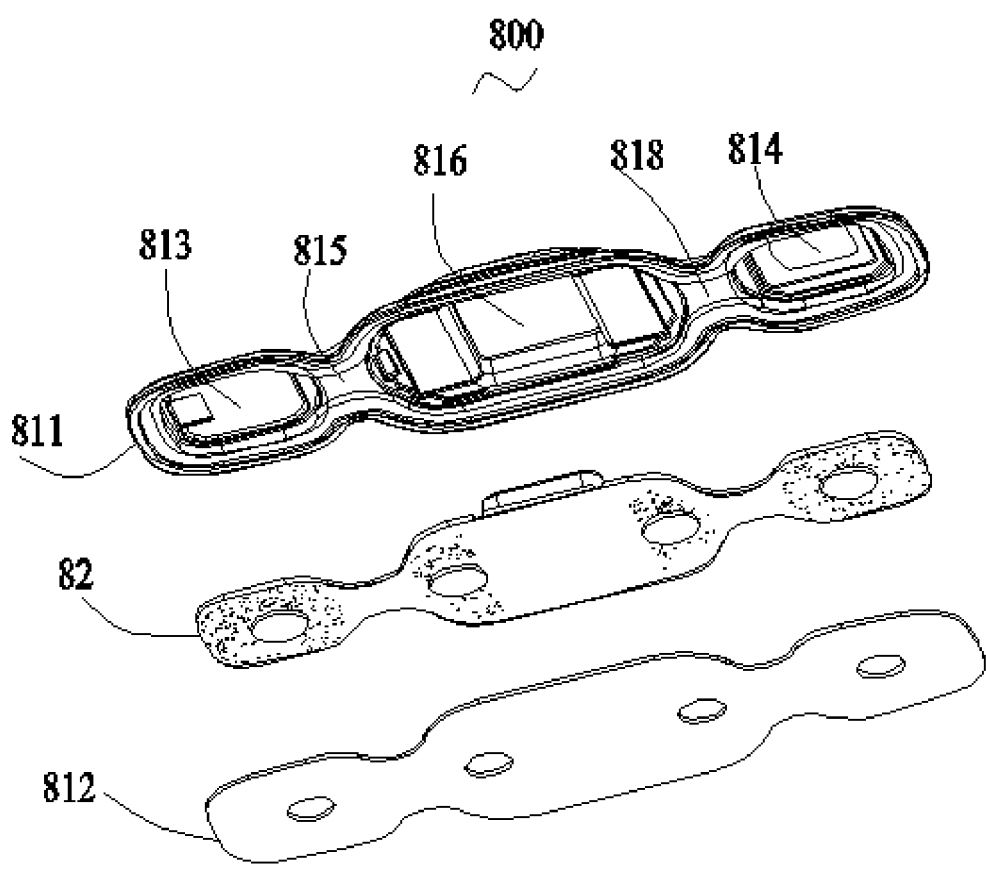
FIG. 3 is another exploded view of the sensor of FIG. 1.

Referring to FIG. 1, the sensor assembly 600 of the present disclosure includes a sensor 800 and a sensor accessory 100. Referring to FIGS. 2 and 3, the sensor 800 includes a housing 81 and a circuit board assembly 82. The housing 81 includes an upper housing 811 and a lower housing 812. The lower housing 812 is substantially in the shape of a flat plate, and four through holes (not numbered) are arranged on the lower housing 812, wherein the through holes may expose electrodes (not shown) located below the circuit board assembly 82, so that the electrodes are connected to four output electrodes (not shown) on the sensor accessory 100. The upper housing 811 and the lower housing 812 cooperate to form a first accommodation cavity 813, a second accommodation cavity 814, a first connection portion 815, a third accommodation cavity 816, and a second connection portion 818. That is to say, the housing 81 is formed with the first accommodation cavity 813, the second accommodation cavity 814, the first connection portion 815, the second connection portion 818 and the third accommodation cavity 816. One end of the third accommodation cavity 816 is connected to the first accommodation cavity 813 via the first connection portion 815, and the other end of the third accommodation cavity 816 is connected to the second accommodation cavity 814 via the second connection portion 818. In other words, the upper housing 811 and the lower housing 812 cooperate to form a plurality of accommodation cavities (namely, the first accommodation cavity 813, the second accommodation cavity 814, and the third accommodation cavity 816). The plurality of accommodation cavities are connected to each other via corresponding connection portions (the first connection portion 815 and the second connection portion 818). The circuit board assembly 82 is arranged between the upper housing 811 and the lower housing 812, and the circuit board assembly 82 is accommodated in the plurality of accommodation cavities formed by the upper housing 811 and the lower housing 812. In other words, the circuit board assembly 82 is accommodated within the first accommodation cavity 813, the second accommodation cavity 814, the first connection portion 815, the second connection portion 818 and the third accommodation cavity 816.

The width (the width in the present disclosure refers to a direction B in FIG. 2) of the first connection portion 815 is significantly less than the width of the first accommodation cavity 813 and the third accommodation cavity 816; the width of the second connection portion 818 is significantly less than the width of the second accommodation cavity 814 and the third accommodation cavity 816; and the first connection portion 815/the second connection portion 818 forms a circular arc transition connection with the two connected accommodation cavities. One advantage of this design lies in that the flexibility of the first connection portion 815 and the second connection portion 818 may be increased, thereby facilitating the motion of the first or second accommodation cavities 813, 814 relative to the third accommodation cavity 816. Between the first connection portion 815 and the second connection portion 818, and the accommodation cavity, a connection stress may be reduced by means of the circular arc transition connection. In addition, a buffer groove 817 is further respectively arranged in a width direction of the first connection portion 815 and the second connection portion 818. Further, the buffer groove 817 is arranged on the upper housing 811. By arranging the buffer groove 817 on the first connection portion 815 and the second connection portion 818, the buffer groove 817 may relieve the stress generated at the time of motion of the first or second accommodation cavities 813, 814 relative to the third accommodation cavity 816.

During use, the sensor 800 may be attached to the skin by means of the sensor accessory 100 for physiological signal monitoring. A plurality of accommodation cavities on the housing 81 of the sensor 800 respectively correspond to different muscle groups, and since different muscle groups of a user have inconsistent motion directions during motion, the sensor assembly 600 will be pulled, such that the deformation between the skin and the sensor 800 is produced to affect the change in skin potential, causing motion artifacts. In the present disclosure, by setting the width of the first connection portion 815 and the second connection portion 818 of the housing 81 to be less than the width of the accommodation cavities to which the two connection portions are connected, and by arranging a buffer groove on the first connection portion 815 and the second connection portion 818, the flexibility of the connection portions is better, and a plurality of accommodation cavities may make a relative motion following the motion of a muscle group without changing the positional relationship with the muscle group. Thus, during the motion of a user, the position of the muscle group detected by the sensor assembly is basically kept fixed, such that the motion artifact caused by the deformation of skin is reduced, the influence of the motion artifact on the monitoring is reduced, and the accuracy of physiological signal monitoring is improved.

Further, the thickness (namely, the length in a direction perpendicular to a plane where the lower housing 812 is located) of the third accommodation cavity 816 is greater than the thickness of the first accommodation cavity 813 and the second accommodation cavity 814, such that the sensor assembly 600 is structured to be slightly thicker in the middle and thinner at both sides. The structure may reduce the friction between the sensor assembly 600 and a user's clothes, increasing comfort while worn. Further, the projected area of the third accommodation cavity 816 in a plane where the circuit board assembly 82 or the lower housing 812 is located is greater than the projected area of the first accommodation cavity 813 and the second accommodation cavity 814 in the plane where the circuit board assembly 82 or the lower housing 812 is located. Therefore, the volume of the third accommodation cavity 816 is greater than the volume of the first accommodation cavity 813 and the second accommodation cavity 814. The structure may make it possible for the center of gravity of the sensor assembly 600 to be at a middle (the third accommodation cavity 816) position, thereby facilitating the attachment of a reference electrode corresponding to the third accommodation cavity 816 on the sensor accessory 100 to the skin. The area of the third accommodation cavity 816 is large, and the reliability of a connection of the reference electrode on the sensor accessory 100 corresponding to the accommodation cavity 816 to the skin during a movement process may be enhanced.

The upper housing 811 and the lower housing 812 may be made from a silica gel material. The silica gel material has good flexibility and good waterproof performance. Other materials having good flexibility and waterproof performance may also be used in some embodiments, which will not be enumerated here. In one embodiment, the upper housing 811 is formed on the lower housing 812 and is closely combined with the lower housing 812 to form a sealed wrap structure, so as to form the overall sealed wrapping for the circuit board assembly 82, thereby effectively protecting the electronic elements on the circuit board assembly 82. In one embodiment, the upper housing 811 and the lower housing 812 may be integrally formed to form the overall sealed wrapping.

Further, the circuit board assembly 82 includes a first measurement circuit board 821, a second measurement circuit board 822, a first FPCB (flexible printed board) 824, a second FPCB 825 and a reference circuit board 823. The first measurement circuit board 821 is accommodated in the first accommodation cavity 813, the second measurement circuit board 822 is accommodated in the second accommodation cavity 814, and the reference circuit board 823 is accommodated in the third accommodation cavity 816. That is to say, the reference circuit board 823 is arranged between the first measurement circuit board 821 and the second measurement circuit board 822. One end of the reference circuit board 823 is connected to the first measurement circuit board 821 via the first FPCB 824, and the other end of the reference circuit board 823 is connected to the second measurement circuit board 822 via the second FPCB 825. The first FPCB 824 is accommodated in the first connection portion 815, and the second FPCB 825 is accommodated in the second connection portion 818. That is to say, a plurality of circuit boards are connected to each other by means of the FPCB, and different circuit boards may make a relative movement under the drive of the corresponding accommodation cavities, so that the flexibility of the sensor assembly 600 is further enhanced.

Further, the reference circuit board 823 includes a first reference circuit board 826, a second reference circuit board 827 and a third FPCB 825, with the first reference circuit board 826 being connected to the first measurement circuit board 821 via the first FPCB 824, the second reference circuit board 827 being connected to the second measurement circuit board 822 via the second FPCB 825, and the first reference circuit board 826 and the second reference circuit board 827 being connected via the third FPCB 830. This structure may ensure that when the third accommodation cavity 816 is deformed at a certain degree due to the motion of the muscle group, the internal first reference circuit board 826 and second reference circuit board 827 may make a certain degree of relative motion, and move as the muscle group and keep the positional relationship with the muscle group unchanged, thus enhancing the stability of the reference circuit board 823. Further, components, such as a battery, a control chip and a wireless transmission assembly, may be mounted on the reference circuit board 823. Furthermore, the components, such as a battery, a control chip and a wireless transmission assembly, may be mounted on the third FPCB 830, so as to make full use of the space of the third accommodation cavity 816. In addition, electronic elements may be placed on the first reference circuit board 826 and the second reference circuit board 827 as much as possible, so as to reduce the layout of the electronic elements on the first measurement circuit board 821 and the second measurement circuit board 822, such that the center of gravity of the sensor is within the third accommodation cavity 816.

Figure 4:
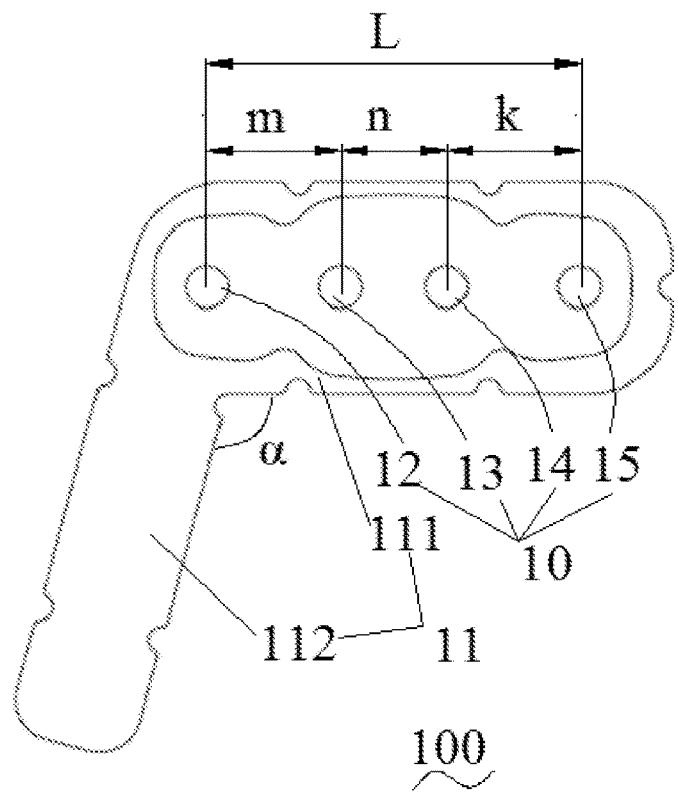
FIG. 4 is a schematic structural diagram of a sensor accessory of FIG. 1.
Figure 5:
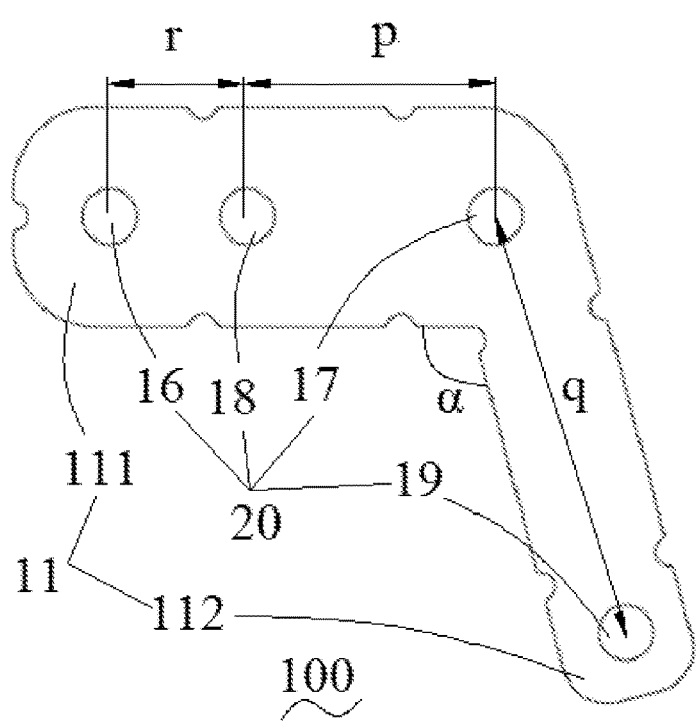
FIG. 5 is another view of the sensor accessory shown in FIG. 4.

In this embodiment, the circuit board assembly 82 includes four electrodes. Specifically, a first electrode (not shown) is arranged at one side of the first measurement circuit board 821 adjacent to the lower housing 812, a fourth electrode (not shown) is arranged at one side of the second measurement circuit board 822 adjacent to the lower housing 812, and a second electrode (not shown) and a third electrode (not shown) are respectively arranged at one side of the first reference circuit board 826 and the second reference circuit board 827 adjacent to the lower housing 812, wherein the first electrode and the second electrode are respectively connected to a first output electrode 12 (as shown in FIG. 4) and a second output electrode 13 (as shown in FIG. 4) on the sensor accessory 100 for receiving signals transmitted by a corresponding first measurement electrode 17 (as shown in FIG. 5) and second measurement electrode 18 (as shown in FIG. 5) on the sensor accessory 100; and the third electrode and the fourth electrode are respectively connected to a third output electrode 14 (as shown in FIG. 4) and a fourth output electrode 15 (as shown in FIG. 4) on the sensor accessory 100 for receiving an electrical signal transmitted by a third input electrode 18 (as shown in FIG. 5) and/or a fourth input electrode 19 (as shown in FIG. 5) on the sensor accessory 100. That is to say, in the sensor assembly 600 of the present disclosure, the sensor 800 includes four electrodes. A through hole (not numbered in the figure) is arranged on the lower housing 812, and the electrode of the sensor 800 may be exposed via the through hole, so as to be connected to the output electrode on the sensor accessory 100.

Referring to FIGS. 4 and 5, in one embodiment of the present disclosure, the sensor accessory 100 includes a base material 11, several output electrodes 10 and several input electrodes 20, wherein the several output electrodes 10 and the several input electrodes 20 are respectively arranged on front and back faces of the base material 11. In one embodiment, the base material 11 is a flat sheet, and the several output electrodes 10 and the several input electrodes 20 are respectively arranged on front and back faces of the base material 11. The several output electrodes 10 include a first output electrode 12, a second output electrode 13, a third output electrode 14 and a fourth output electrode 15, and the several input electrodes 20 at least include a first input electrode 17, a third input electrode 16 and a second input electrode 18. The first output electrode 12, the second output electrode 13, the third output electrode 14 and the fourth output electrode 15 are sequentially arranged on one side of the base material 11. The first input electrode 17, the second input electrode 18 and the third input electrode 16 are sequentially arranged on the other side of the base material 11. The first input electrode 17 is electrically connected to the first output electrode 12. The third input electrode 16 is electrically connected to the fourth output electrode 15. The second input electrode 18 is electrically connected to the second output electrode 13 and/or the third output electrode 14. A center distance L between the first input electrode 17 and the third input electrode 16 is greater than or equal to 60 mm (millimeters).

In one embodiment, during use, a side (namely, the back face) on which the input electrodes 20 are located is attached to human skin, and the several input electrodes 20 are respectively in contact with the human skin. These input electrodes 20 are divided, according to functions, into electrodes having different functions, with the second input electrode 18 being a reference electrode, and the first input electrode 17 and the third input electrode 16 being measurement electrodes. A loop is formed by means of the measurement electrodes and the reference electrode to detect physical sign parameters of a human body, for example, an electrocardiogram signal. The first input electrode 17 transmits the detected physical sign parameters of the human body to the first output electrode 12, and the third input electrode 16 transmits the detected physical sign parameters of the human body to the fourth output electrode 15.

In one embodiment, the sensor accessory 100 is used to cooperate with the above-mentioned sensor 800, and the sensor 800 may cooperate with an electrocardiogram sensor (not shown) to conduct the collected electrocardiogram signals to the electrocardiogram sensor. In the electrocardiogram sensor, there is a certain requirement for the distance between sites of a human body to be collected, namely, a center distance between the first input electrode 17 and the third input electrode 16 as the measurement electrodes would influence the collected electrocardiogram signals. To obtain relatively stable and accurate electrocardiogram, numerous tests are made, and a part of experimental data is as follows:

(1) when a center distance between the first input electrode and the third input electrode may be 40 mm, the amplitude of electrocardiogram signal lead-I may be 1.7 mV, the amplitude of lead-II may be 1.8 mV (millivolt), and the amplitude of lead-III may be 2.6 mV;

(2) when the center distance between the first input electrode and the third input electrode may be 60 mm, the amplitude of electrocardiogram signal lead-I may be 1.9 mV, the amplitude of lead-II may be 1.9 mV, and the amplitude of lead-III may be 2.6 mV;

(3) when the center distance between the first input electrode and the third input electrode may be 80 mm, the amplitude of electrocardiogram signal lead-I may be 2.1 mV, the amplitude of lead-II may be 1.6 mV, and the amplitude of lead-III may be 2.8 mV;

(4) when the center distance between the first input electrode and the third input electrode may be 90 mm, the amplitude of electrocardiogram signal lead-I may be 2.0 mV, the amplitude of lead-II may be 1.8 mV, and the amplitude of lead-III may be 2.3 mV;

(5) when the center distance between the first input electrode and the third input electrode may be 120 mm, the amplitude of electrocardiogram signal lead-I may be 2.1 mV, the amplitude of lead-II may be 1.7 mV, and the amplitude of lead-III may be 2.7 mV;

(6) when the center distance between the first input electrode and the third input electrode may be 140 mm, the amplitude of electrocardiogram signal lead-I may be 2.2 mV, the amplitude of lead-II may be 1.7 mV, and the amplitude of lead-III may be 2.7 mV; and (7) when the center distance between the first input electrode and the third input electrode may be 180 mm, the amplitude of electrocardiogram signal lead-I may be 2.1 mV, the amplitude of lead-II may be 1.6 mV, and the amplitude of lead-III may be 2.0 mV.

Figure 6:
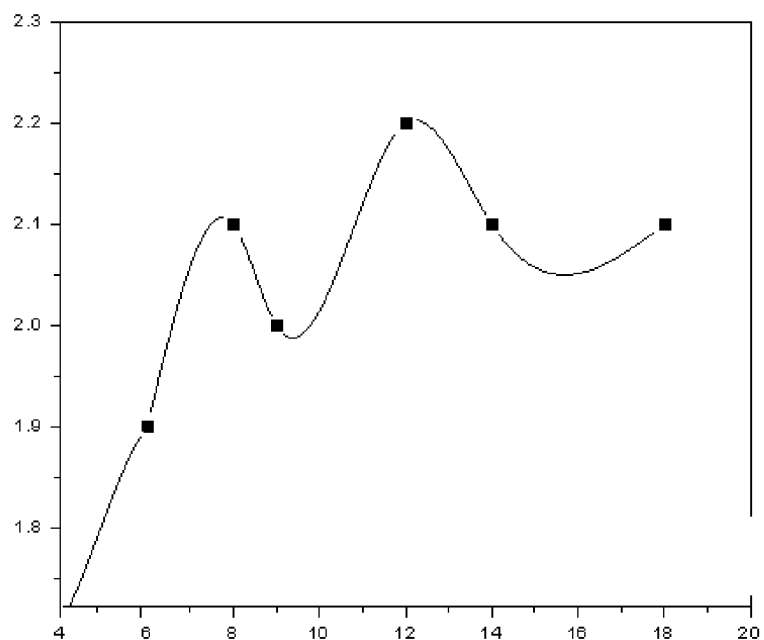
FIG. 6 is a relationship graph of the amplitude of lead-I and two input electrodes.

Since the intensity of the electrocardiogram signal is proportional to the amplitude thereof, the amplitude of electrocardiogram signal lead-I above is represented as FIG. 6 by a statistical graph. It can be seen from FIG. 6 that, when the center distance between the first input electrode and the third input electrode is greater than or equal to 80 mm, the intensity of the electrocardiogram signal basically remains unchanged. In consideration of the experimental error factors, in order to ensure that relatively stable electrocardiogram signals can be collected, it should be ensured that a center distance L between the first input electrode 17 and the third input electrode 16 is greater than or equal to 60 mm. It can be understood that, for the electrocardiogram sensor, a position where the sensor accessory 100 is attached is a prethoracic position near the heart, and in consideration of the limitation on the prethoracic width of a human body, the center distance between the first input electrode 17 and the third input electrode 16 needs to be further defined. In one embodiment, a center distance L between the first input electrode 17 and the third input electrode 18 should be less than 180 mm. That is to say, the center distance L between the first input electrode 17 and the third input electrode 16 is between 60 and 180 mm. Within this range, the change in the center distance between the first input electrode 17 and the third input electrode 16 does not greatly affect the intensity of the electrocardiogram signals, and the obtained electrocardiogram is relatively stable.

As described above, the first input electrode 17, the third input electrode 16 and the second input electrode 18 are arranged on a side of the base material 11 for contact with human skin for collecting the electrocardiogram signals of the human body and then transmitting the signals to the corresponding output electrodes 20 arranged on the other side of the base material 11, and the output electrodes 20 are in contact with four electrodes on the sensor 800 adapted to the sensor accessory 100, so as to transmit the collected electrocardiogram signals to the sensor 800 for further processing. That is to say, the four electrodes on the sensor 800 correspond to the four output electrodes 20 on the base material 11 on a one-to-one basis, and receive the electrocardiogram signals output by the four output electrodes 20. Obviously, the electrocardiogram sensor further transmits the received electrocardiogram signals to a computing apparatus in a wireless or wired manner, which will not be described here because of irrelevance with the improvement of the present disclosure.

In one embodiment, a center distance m between the first output electrode 12 and the second output electrode 13 may be 18-22 mm, a center distance n between the second output electrode 13 and the third output electrode 14 may be 22-25 mm, and a center distance k between the third output electrode 14 and the fourth output electrode 15 may be 18-22 mm. Typically, the positions of the output electrodes on the base material 11 correspond to those of contacts on the sensor 800 on a one-to-one basis, and thus the definitions above are further made to adapt to the sensor 800.

Further, continuously referring to FIGS. 4 and 5, the sensor accessory 100 in the present disclosure may be a dual-channel electrocardiogram sensor accessory. The base material 11 may be substantially of an L-shaped structure and includes a first long arm 111 and a second long arm 112. The input electrodes 20 further include a fourth input electrode 19. The second input electrode 18 is electrically connected to the third output electrode 14. The fourth input electrode 19 is electrically connected to the second output electrode 13. The first input electrode 17, the second input electrode 18 and the third input electrode 16 are sequentially arranged on one side of the first long arm 111 of the base material 11, and the fourth input electrode 19 is arranged on the same side of the second long arm 112 of the base material. The first output electrode 12, the second output electrode 13, the third output electrode 14 and the fourth output electrode 15 are arranged on the other side of the first long arm 111. The positions of the first output electrode 12, the third output electrode 14 and the fourth output electrode 15 correspond to the positions of the first input electrode 17, the second input electrode 18 and the third input electrode 16 on a one-to-one basis. Further, in this embodiment, the fourth input electrode 19 is a measurement electrode; the first input electrode 17, the second input electrode 18 and the third input electrode 16 are linearly arranged, on the first long arm 111, toward a direction gradually away from the second long arm 112; and the fourth input electrode 19, the first input electrode 17 and the third input electrode 16 are not on the same straight line.

In this embodiment, by arranging the three measurement electrodes that are not on the same straight line, each of the measurement electrodes may measure one measurement voltage. Therefore, in this embodiment, at least two signal voltage differences may be obtained (three voltage differences can be formed at most), such that the electrocardiogram signals of the human body may be measured from two cross-sectional directions. Therefore, the sensor accessory is referred to as dual-channel electrocardiogram sensor accessory.

In one embodiment, a center distance q between the fourth input electrode 19 and the first input electrode 17 is 70-90 mm. Within this range, it may be ensured that the amplitude of the electrocardiogram signal collected by the fourth input electrode 19 is relatively large but relatively stable, and is convenient for observation. In addition, this length is designed such that when the first input electrode 17 is placed at an upper edge of a rib, the fourth input electrode 19 may reach a lower end of the heart, so that the sensor accessory 100 may span the entire heart, ensuring that the electrocardiogram signals collected by the first input electrode 17 and the fourth input electrode 19 may reflect the condition of the larger cross section of the heart so as to more accurately measure the electrocardiogram signals of the heart.

In one embodiment, an included angle α between the first long arm 111 and the second long arm 112 of the base material 11 may be 90°-150°. In order to enhance the diversity of the electrocardiogram signals collected by the sensor accessory 100, the second input electrode 18 should be kept from the fourth input electrode 19 at a certain linear distance, and where the center distance q between the fourth input electrode 19 and the first input electrode 17 may be 70-90 mm, it is necessary to define an included angle between two arms of the base material 11. At the same time, for female users, when an electrocardiogram signal is collected, the breasts should be avoid in the process of the attachment of the sensor accessory 100 as much as possible, so as to increase the wearing comfort for the female users. Therefore, after comprehensive considerations, it should be ensured that the included angle α of the L-shaped base material 11 may be 90°-150°.

In one embodiment, a center distance r between the second input electrode 18 and the third input electrode 16 may be 18-22 mm. A center distance p between the second input electrode 18 and the first input electrode 17 may be 40-50 mm.

Figure 7:
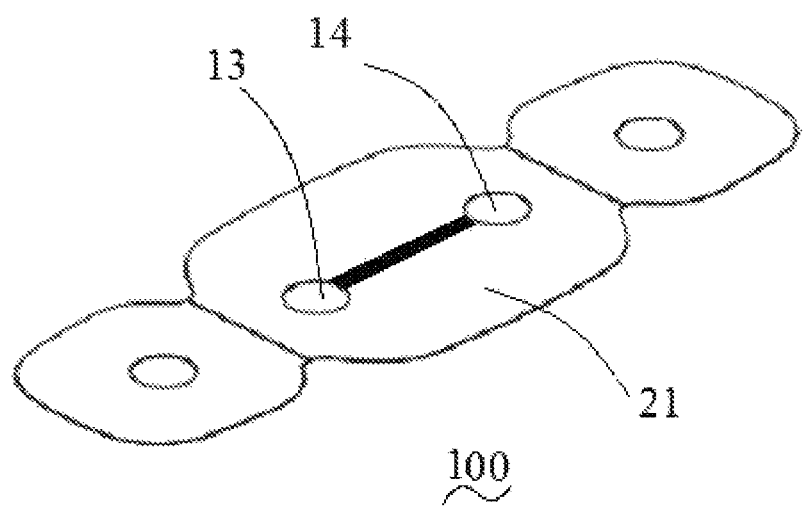
FIG. 7 is a schematic structural diagram of the sensor accessory of FIG. 1.
Figure 8:
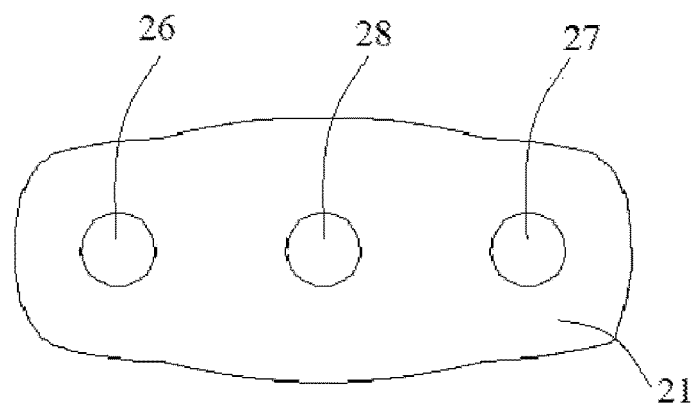
FIG. 8 is another view of a sensor accessory shown in FIG. 7.

FIGS. 7 and 8 are schematic diagrams of the sensor accessory 100 in one embodiment of the present disclosure. An electrocardiogram sensor adapted to the sensor accessory 100 in this embodiment is identical to the electrocardiogram sensor adapted to the sensor accessory 100 in the first embodiment. That is, in this embodiment, the sensor accessory 100 is fitted with the same sensor 800 as that in the previous embodiment. The sensor accessory 100 of this embodiment is a single-channel electrocardiogram sensor accessory. For the output electrodes of the sensor accessory 100, since the same sensor 800 is employed, the arrangement of the output electrodes on the base material 21 is identical to that in the above-mentioned embodiment. The difference between the sensor accessory 100 of this embodiment and that of the first embodiment lies in that the base material 21 is substantially in a "linear" shape. The second input electrode 28 is arranged between the first input electrode 26 and the third input electrode 27, and is electrically connected to the second output electrode 13 and the third output electrode 14 at the same time. Specifically, the second input electrode 28 may be electrically connected to the second output electrode 13 and the third output electrode 14 via a wire; or the second output electrode 13 and the third output electrode 14 are shorted and then electrically connected to the second input electrode 28. Further, the electrical connection described in the present disclosure may be realized by means of physical crimping, conductive double-sided adhesive connection, wire connection, etc.

In one embodiment, the second input electrode 28 is arranged at a middle position between the first input electrode 26 and the third input electrode 27.

Figure 9:
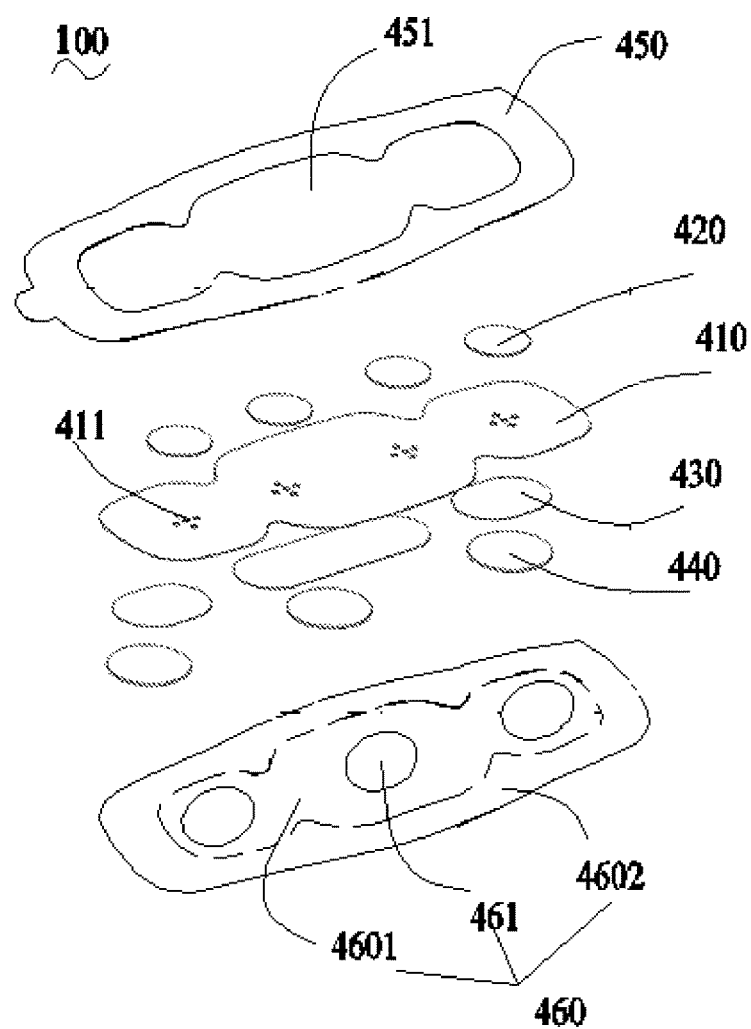
FIG. 9 is a schematic exploded structure diagram of the sensor accessory of FIG. 1.

FIG. 9 is a schematic exploded structure diagram of the sensor accessory 100 in the sensor assembly 600. The sensor accessory 100 further includes a base layer 410, a conductive layer 420, a barrier layer 430 and a conductive gel 440. The conductive layer 420 is formed on one side of the base layer 410, and the barrier layer 430 is formed on the other side of the base layer 410. That is to say, the base layer 410 is arranged between the conductive layer 420 and the barrier layer 430. The conductive gel 440 is attached to a side of the barrier layer 430 which is not in contact with the base layer 410. The base layer 410 is made of a non-conductive material, and the conductive layer 420, the barrier layer 430 and the conductive gel are made of conductive materials. A conductive via hole 411 for penetrating two faces of the base layer 410 is further arranged on the base layer 410, and the conductive layer 420 is electrically connected to the barrier layer 430 via a conductive medium in the conductive via hole 411. The conductive layer 420 is further electrically connected to the conductive gel 440 attached to the barrier layer 30 via the barrier layer 430 and the conductive via hole 411. The conductive via hole 411 is formed by coating a conductive medium on a hole wall of the through hole penetrating two faces of the base layer 410, or is formed by injecting a conductive medium in the through hole.

In this embodiment, the material of the conductive layer 420 is conductive carbon ink, and in one embodiment, the material of the conductive layer 420 may be silver or silver chloride (Ag/AgCl).

Further, the conductive gel 440 may be a liquid electrolyte gel, and may also be a solid hydrocolloid gel. During the use of the sensor accessory 100, a side where the conductive gel 440 is located just faces the human skin to collect physical sign parameters of the human body, such as an electrocardiogram signal and temperature. The conductive gel 440 has a higher salt content to maximize the signal quality and a lower impedance. Meanwhile, because of a higher salt content of the conductive gel 440, its shelf life is short and a chemical reaction is prone to occur. If the conductive gel 440 is directly in contact with the conductive layer 420, the conductive performance of the conductive layer 420 would be affected. Therefore, the conductive layer 420 should be separated from the conductive gel 440 by means of the barrier layer 430, thereby avoiding the direct contact between the conductive layer 420 and the conductive gel 440. The barrier layer 430 may be directly printed onto the base layer 410, typically using a silver or silver chloride (Ag/AgCl) material. The barrier layer 430 typically has a thickness of less than ten microns to more than ten but less than twenty microns. The barrier layer 430 may transmit electrical signals collected by the conductive gel 440 to the conductive layer 420.

Further specifically, the conductive medium in the conductive via hole 411 may be silver or silver chloride (Ag/AgCl) or carbon ink, or may also be other materials that may electrically connect the conductive layer 420 and the barrier layer 430.

The sensor accessory 100 of the present disclosure makes it possible to respectively place a conductive layer and a conductive gel layer at two sides of a base layer, a barrier layer is further arranged between the conductive gel layer and the substrate, and a via hole is arranged on a base layer to electrically connect the conductive layer and the barrier layer. By means of this structure, a vertical electrical connection between the sensor and the sensor accessory 100 may be realized without bending the base layer, such that the overall thickness of the sensor assembly is reduced; meanwhile, the abnormalities, such as circuit breakage, of the base layer caused by bending are avoided, and the stability of the sensor accessory 100 is improved.

Furthermore, the projection of the conductive gel 440 on the barrier layer 430 is contained in the barrier layer 430. That is to say, the area of the conductive gel 440 is less than the area of the barrier layer 430 and is attached within the barrier layer 430, and the conductive gel 440 only covers a part of the barrier layer 430. As such, the conductive gel 440 is further prevented from coming into contact with the other conductive media.

Further, the base layer 410 is a flexible, non-conductive material. In one embodiment, a flexible insulator, such as a flexible PET, foam back or non-woven material, may be used.

Further, the sensor accessory 100 further includes a connection layer 460. The connection layer 460 includes a connection region 4601 (a region formed by means of surrounding by a dotted line in FIG. 9) and an edge region 4602. One side of the base layer 410 having the barrier layer 430 and the conductive gel 440 is attached to the connection region 4601 of the connection layer 460, such that the conductive gel 440 just faces the connection layer 460. The connection region is further provided with a communication hole 461, wherein the size and position of the communication hole 461 correspond to those of the conductive gel 440, and the conductive gel 440 may be connected to the outside (electrode) via the communication hole 461. Further In one embodiment, in order to further ensure the wearing comfort, the thickness of the edge region 4602 of the connection layer 460 should be less than 0.1 mm, and the thickness of the connection region 4601 thereof may be slightly greater than 0.1 mm. The connection layer 460 may be a flexible film. The film has good flexibility and attachment performance. In one embodiment, the connection layer 460 may be made of a polyurethane film or silica gel film material. The polyurethane film material has excellent mechanical performances, such as skin-friendliness, wear resistance and flex resistance, and additionally further has the characteristics of good aging resistance and mildew resistance.

Further, the sensor accessory 100 further includes a support layer 450, wherein the support layer 450 is arranged on one side of the base layer 410 having the conductive layer 420 and cooperates with the connection layer 460 to form an accommodation space for accommodating the base layer 410 formed with the conductive layer 420, the barrier layer 430 and the conductive gel 440 therein. Specifically, the edge region 4602 of the connection layer 460 and the support layer 450 are connected to each other by means of vacuum adsorption so as to form the accommodation space. A through hole 451 is further arranged on the support layer 450, and the conductive layer 420 may communicate with the outside via the through hole 451, so as to be electrically connected to the sensor 800 that cooperates with the sensor accessory 100. Further specifically, the shape of the through hole 451 is the same as that of the base layer 410, and the shape of the through hole 451 coincides with that of the base layer 410. The sensor 800 may be fixed onto the connection layer 460 by penetrating the through hole 451, and the sensor may be electrically connected to the conductive layer 420 via the through hole 451 so as receive the signals collected by the conductive gel of the sensor accessory 100.

The support layer 450 has a size substantially the same as the size of the connection layer 460 and has a certain hardness, and the support layer 450 may play the role of flattening the connection layer 460. Since the connection layer 460 has a relatively thin thickness and has a certain flexibility, a curling phenomenon would occur under normal conditions. When the sensor assembly 600 needs to be worn (attached) to the skin, the connection layer 460 needs to be flattened first, resulting in a relatively complicated process of attaching the sensor assembly 600. The connection layer 460 may be pre-flattened by adding the support layer 50 fixedly connected to the connection layer 460, which simplifies the attachment process of the sensor assembly 600. After the wearing process of the sensor assembly 600 is completed, the support layer 450 may be torn off from the connection layer 460, and since the two are merely fixedly connected by means of vacuum adsorption, the tearing process is relatively simple.

Specifically, as shown in FIG. 9, the conductive layer 420 is divided into four independent regions, with one output electrode (such as the first output electrode 12, the second output electrode 13, the third output electrode 14 and the fourth output electrode 15 in FIG. 4) being arranged on each of the regions; and each output electrode corresponds to one electrode (namely, electrodes respectively located on the first measurement circuit board 821, the second measurement circuit board 822, the first reference circuit board 826 and the second reference circuit board 827) on the circuit board assembly 82. The four regions of the conductive layer 420 are arranged in parallel on one side of the base layer 410; the barrier layer 430 is divided into three independent regions (single-channel sensor accessories), and the three regions of the barrier layer 430 are arranged in parallel on the other side of the base layer 410; and there are three conductive gels 440, which are respectively attached to the three regions of the barrier layer 430, and one input electrode is arranged on each of the conductive gels 440 for collecting electrical signals of the human body. That is, the first input electrode 26, the second input electrode 27 and the third input electrode 28 in FIG. 8 are respectively arranged on the three conductive gels 440. The area of each of the conductive gels 440 attached to the corresponding regions of the barrier layer 430 is less than the area of the attached region. A region of the barrier layer 430 in the middle has an area substantially equal to that of two regions of the conductive layer 420 in the middle and has a position substantially corresponding to that of two regions of the conductive layer, and is electrically connected to the two regions of the conductive layer 420 in the middle via the corresponding conductive via hole 411. The positions of regions of the barrier layer 430 at two ends substantially correspond to the positions of regions of the conductive layer 420 at two ends, and the regions of the barrier layer 430 at two ends are respectively and electrically connected to the regions of the conductive layer 420 at two ends via the conductive via holes 411.

Thus, the conductive gel 440 located in the middle are simultaneously and electrically connected to the two regions of the conductive layer 420 in the middle, and the two conductive gels 440 at two ends are respectively and electrically connected to the two regions of the conductive layer 420 at two ends.

It can be understood that in some embodiments, the conductive layer 420 and the barrier layer 430 may each include four independent regions (dual-channel sensor accessories), and there are four conductive gels 440. One input electrode (namely, the first input electrode 17, the second input electrode 16, the third input electrode 18 and the fourth input electrode 19 in FIG. 5) is arranged on each of the conductive gels 440 for a corresponding connection with the four electrodes on the sensor 800 on a one-to-one basis. Each of the conductive gels 440 is attached to a corresponding region of the barrier layer 430 or is connected to the corresponding region of the barrier layer 430 by means of a wire. The area of the conductive gel 440 attached to the corresponding region of the barrier layer 430 is less than the area of the attached region. Each of the regions of the barrier layer 430 is electrically connected to one region of the conductive layer 420 arranged on one side of the base layer 410 via the conductive via hole 411. Specifically, the four regions of the conductive gel 440 have positions that may be adjusted according to actual needs, and then may be connected to the corresponding regions of the barrier layer 430 by means of wires.

Figure 11:
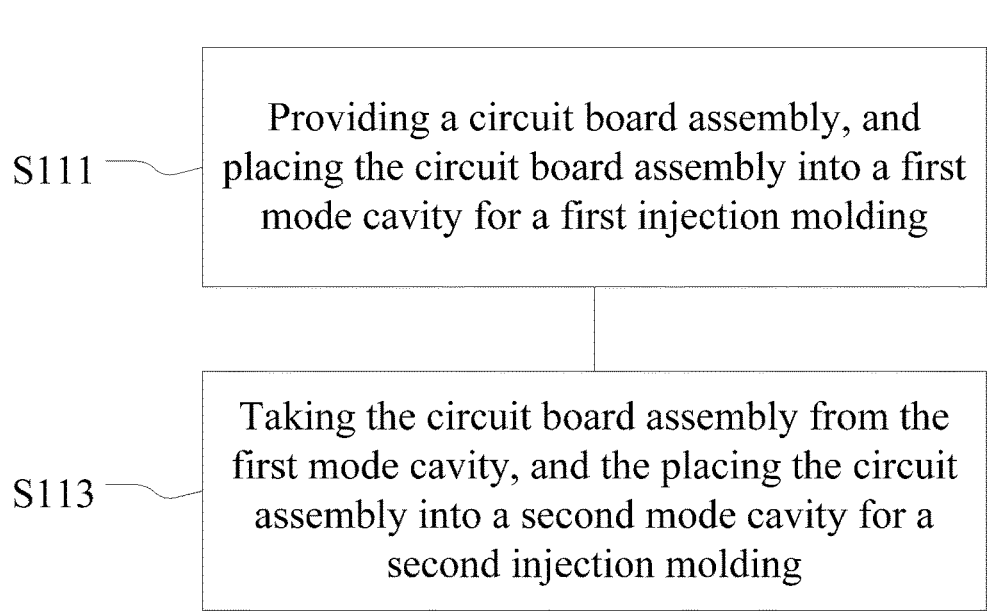
FIG. 11 is an injection molding flowchart of the sensor of FIG. 1.

As shown in FIG. 11, the present disclosure further provides a method for manufacturing a sensor assembly. The method may include:

step S111: referring to FIGS. 1, 2 and 10, firstly, providing a circuit board assembly, and placing the circuit board assembly into a first mold cavity (not shown) for a first injection molding to form a lower housing below the circuit board assembly, wherein the lower housing having a first bottom side 8121, a second bottom side 8122, a third bottom side 8123, a first connection bottom side 8124 and a second connection bottom side 8125.

Figure 10:
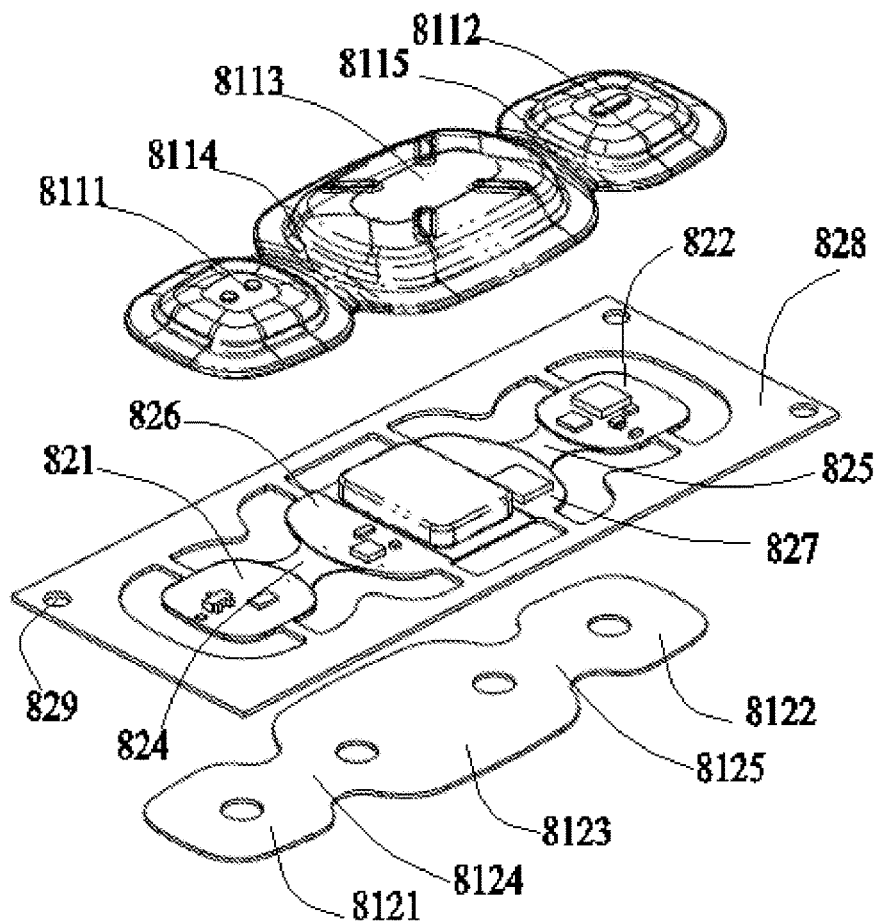
FIG. 10 is a schematic diagram of an injection molding process of the sensor of FIG. 1.

Specifically, as shown in FIGS. 1, 2 and 10, after the first injection molding is performed on the circuit board assembly 82, the first bottom side 8121 is formed below the first measurement circuit board 821, the second bottom side 8122 is formed below the second measurement circuit board 822, the third bottom side 8123 is formed below the reference circuit board 823, the first connection bottom side 8124 is formed below the first FPCB 824, and the second connection bottom side 8125 is formed below the second FPCB 825.

step S113: then, taking the circuit board assembly 82 from the first mold cavity, and then placing the circuit board assembly into a second mold cavity for a second injection molding to form an upper housing on the lower housing, wherein the upper housing 811 having a first top side 8111, a second top side 8112, a first connection top side 8114, a second connection top side 8115 and a third top side 8113, wherein the lower housing 812 and the upper housing 811 closely cooperate to form a housing. Specifically, a first accommodation cavity is formed between the first top side 8111 and the first bottom side 8121, a second accommodation cavity is formed between the second top side 8112 and the second bottom side 8122, a third accommodation cavity is formed between the third top side 8113 and the third bottom side 8123, the first connection bottom side 8124 and the first connection top side 8114 form a first connection portion 815, and the second connection bottom side 8125 and the second connection top side 8115 form a second connection portion 818, such that the first measurement circuit board 821 of the sensor assembly 82 is accommodated within the first accommodation cavity, the second measurement circuit board 822 thereof is accommodated within the second accommodation cavity, and the reference circuit board 823 is accommodated within the third accommodation cavity; and the first FPCB 824 is accommodated within the first connection portion 815. The second FPCB 825 is accommodated within the second connection portion 818. That is to say, the circuit board assembly 82 is completely wrapped by the upper housing 81 and the lower housing 82 by means of injection molding twice. After the injection molding twice, there is no parting line between the upper housing and the lower housing, such that the sensor assembly is more comfortable to wear, has a better airtightness, and also looks more aesthetic.

Further, the method for manufacturing a sensor assembly further includes the steps of: prior to performing the first injection molding, connecting the circuit board assembly 82 to an outer frame 828, such that the circuit board assembly is fixed the position within the first mold cavity by means of the outer frame 828. Specifically, a positioning hole 829 is arranged on the outer frame 828, and after the positioning with a positioning mechanism in the first mold cavity through the positioning hole 829 and the injection molding are completed, the circuit board assembly 82 is ejected from the first mold cavity.

Further, the method for manufacturing a sensor assembly further includes the steps of: After the first injection molding is completed, the circuit board assembly 82 is taken from the first mold cavity, and the outer frame 828 is removed from the circuit board assembly 82. Since the lower housing 812 and the circuit board assembly 82 have been fixed together at this time, same may be aligned with a positioning mechanism in a second mold cavity through a hole on the lower housing 812 so as to fix the circuit board assembly 82, thus completing the second injection molding process.

It can be understood that the injection molding in the present disclosure is made by using a liquid silica gel material.

The embodiments of the present disclosure are introduced in detail above. The principles and implementations of the present disclosure are illustrated herein by applying specific examples, and the description of the embodiments above is merely used to help understand the method of the present disclosure and the core ideas thereof. Meanwhile, for a person of ordinary skill in the art, there are changes in both of the specific implementations and the application range according to the ideas of the present disclosure. Thus, the contents of the description should not be construed as limitations but rather examples.

What is claimed is:

1. A sensor assembly, comprising a housing and a circuit board assembly, wherein the housing comprises a first accommodation cavity, a second accommodation cavity, a first connection portion, a second connection portion and a third accommodation cavity, with the first connection portion being connected to the first accommodation cavity and one end of the third accommodation cavity, and the second connection portion being connected to the second accommodation cavity and the other end of the third accommodation cavity; the circuit board assembly is accommodated within the first accommodation cavity, the second accommodation cavity, the first connection portion, the second connection portion and the third accommodation cavity, with the widths of the first connection portion and the second connection portion being less than the widths of the first accommodation cavity, the second accommodation cavity and the third accommodation cavity; and the first connection portion and the second connection portion are each provided with a buffer groove along the width direction,
> wherein the circuit board assembly comprises a first measurement circuit board accommodated within the first accommodation cavity, a second measurement circuit board accommodated within the second accommodation cavity, a reference circuit board accommodated within the third accommodation cavity, a first flexible printed circuit board (FPCB) accommodated within the first connection portion and a second FPCB accommodated within the second connection portion, with one end of the reference circuit board being connected to the first measurement circuit board via the first FPCB, and the other end of the reference circuit board being connected to the second measurement circuit board via the second FPCB, and
> wherein the reference circuit board comprises a first reference circuit board, a second reference circuit board and a third FPCB, with the first reference circuit board being connected to the first measurement circuit board, the second reference circuit board being connected to the second measurement circuit board, and the first reference circuit board and the second reference circuit board being connected via the third FPCB.

2. The sensor assembly of claim 1, further comprising a battery, wherein the battery is arranged on the third FPCB.

3. The sensor assembly of claim 1, wherein the housing comprises an upper housing and a lower housing, with the upper housing and the lower housing mating to form the first accommodation cavity, the second accommodation cavity, the first connection portion, the second connection portion and the third accommodation cavity; the circuit board assembly is arranged between the upper housing and the lower housing; and the buffer groove is arranged on the upper housing.

4. The sensor assembly of claim 1, further comprising a sensor accessory, wherein the sensor accessory comprises a base material, and a first output electrode, a second output electrode, a third output electrode and a fourth output electrode which are sequentially arranged on one side of the base material, and a first input electrode, a second input electrode and a third input electrode which are sequentially arranged on the other side of the base material, with the first input electrode being electrically connected to the first output electrode, the third input electrode being electrically connected to the fourth output electrode, the second input electrode being electrically connected to the second output electrode and/or the third output electrode, and a center distance between the first input electrode and the third input electrode being greater than or equal to 60 mm.

5. The sensor assembly of claim 1, further comprising a sensor accessory, wherein the sensor accessory comprises a base layer, a conductive layer formed on one side of the base layer, a barrier layer formed on the other side of the base layer, and a conductive gel attached to the barrier layer, with a conductive via hole penetrating the two sides of the base layer being arranged on the base layer, and the conductive layer being electrically connected to the barrier layer via the conductive via hole.

6. The sensor assembly of claim 1, wherein the sensor assembly comprises at least one of conditions of: the third accommodation cavity is thicker than the first accommodation cavity and the second accommodation cavity; and a projection area of the third accommodation cavity in a plane where the circuit board assembly is located is greater than the projected area of the first accommodation cavity in the plane where the circuit board assembly is located, and the projected area of the third accommodation cavity in the plane where the circuit board assembly is located is greater than the projected area of the second accommodation cavity in the plane where the circuit board assembly is located.

7. The sensor assembly of claim 3, wherein the sensor assembly comprises at least one of conditions of: the upper housing and the lower housing are integrally formed; and the upper housing and the lower housing are made from a silica gel material.

8. The sensor assembly of claim 4, wherein the sensor assembly comprises at least one of conditions of: the second output electrode and the third output electrode are electrically connected to the second input electrode simultaneously; and the second output electrode and the third output electrode are electrically connected to the second input electrode simultaneously, and the second input electrode is arranged between the first input electrode and the third input electrode.

9. The sensor assembly of claim 4, further comprising a fourth input electrode arranged on the other side of the base material, wherein the fourth input electrode is electrically connected to the second output electrode; the second input electrode is electrically connected to the third output electrode; the base material is of an L shape, and the base material comprises a first long arm and a second long arm; the first input electrode, the second input electrode and the third input electrode are sequentially arranged on the first long arm along a direction far away from the second long arm; and the fourth input electrode is arranged on the second long arm of the base material.

10. The sensor assembly of claim 5, wherein the sensor accessory further comprises a connection layer, with a communication hole being arranged on the connection layer, and the side of the base layer provided with the conductive gel is attached to the connection layer, with the conductive gel being exposed via the communication hole.

11. The sensor assembly of claim 5, wherein a projection of the conductive gel on the barrier layer is contained in the barrier layer.

12. The sensor assembly of claim 9, wherein the sensor assembly comprises at least one of conditions of: a center distance between the fourth input electrode and the first input electrode is 70-90 mm; and an included angle between the first long arm and the second long arm is 90°-150°.

13. The sensor assembly of claim 10, wherein the sensor accessory further comprises a support layer, with the support layer being detachably attached on the connection layer, a through hole being arranged on the support layer, and the conductive layer being exposed via the through hole.

14. The sensor assembly of claim 13, wherein the support layer and the connection layer are fixed to each other by means of vacuum adsorption.

* * * * *